(12) United States Patent
Adkins et al.

(10) Patent No.: US 9,868,930 B2
(45) Date of Patent: Jan. 16, 2018

(54) PH SENSOR FOR SINGLE USE EQUIPMENT (71) Applicant: Rosemount Analytical Inc., Irvine, CA (US)

(72) Inventors: Michalle Jane Alleman Adkins, Morgantown, PA (US); Chang-Dong Feng, Long Beach, CA (US)

(73) Assignee: Rosemount Analytical Inc., Irvine, CA (US)

( * ) Notice: Subject to any disclaimer, the term of this patent is extended or adjusted under 35 U.S.C. 154(b) by 0 days.

(21) Appl. No.: 15/136,188

(22) Filed: Apr. 22, 2016

(65) Prior Publication Data

US 2016/0312170 A1    Oct. 27, 2016

Related U.S. Application Data

(60) Provisional application No. 62/152,146, filed on Apr. 24, 2015.

(51) Int. Cl.
| | |
|---|---|
| *B01L 9/00* | (2006.01) |
| *G01N 15/06* | (2006.01) |
| *G01N 33/00* | (2006.01) |
| *G01N 33/48* | (2006.01) |
| *C12M 1/34* | (2006.01) |
| *C12M 1/00* | (2006.01) |
| *G01N 27/28* | (2006.01) |

(52) U.S. Cl.
CPC ............ *C12M 41/26* (2013.01); *C12M 23/28* (2013.01); *G01N 27/283* (2013.01)

(58) Field of Classification Search
CPC .......... B01L 9/00; G01N 15/06; G01N 33/00; G01N 33/48

USPC .... 422/68.1, 82.03, 82.01, 560, 565; 436/43
See application file for complete search history.

(56) References Cited

U.S. PATENT DOCUMENTS

| | | |
|---|---|---|
| 7,924,017 B2 | 4/2011 | Ammann et al. |
| 7,972,495 B1 | 7/2011 | Millar et al. |
| 8,123,397 B2 | 2/2012 | Baumfalk et al. |
| (Continued) | | |

FOREIGN PATENT DOCUMENTS

WO    WO2008016411 A1    2/2008

OTHER PUBLICATIONS

International Search Report and Written Opinion for International Application No. PCT/US2016/028884, dated Jul. 28, 2016, date of filing: Apr. 22, 2016, 16 pages.

*Primary Examiner* — Brian J Sines
(74) *Attorney, Agent, or Firm* — Christopher R. Christenson; Kelly, Holt & Christenson PLLC (57) ABSTRACT

A single use pH sensor housing for a single use container is provided. The single use pH sensor housing includes a compartment configured to house a single use pH sensor. In one embodiment, the single use pH sensor housing comprises an actuator configured, when actuated, to transition the single use pH sensor from a storage position to a deployed position. In the storage position, the pH sensor is in fluidic contact with a buffer solution. In the deployed position, the single use pH sensor is in fluidic contact with an interior of the single use container. During the transition from the storage position to the deployed position, the buffer solution moves from a sensor portion of the compartment to a storage portion of the compartment such that the buffer solution is isolated from contact with the interior of the single use container.

10 Claims, 12 Drawing Sheets

(56) References Cited

U.S. PATENT DOCUMENTS

| | | |
|---|---|---|
| 8,252,582 B2 | 8/2012 | Baumfalk et al. |
| 2005/0163667 A1 | 7/2005 | Krause |
| 2007/0159920 A1* | 7/2007 | Baumfalk ............... B01F 7/162 366/152.4 |
| 2007/0252290 A1* | 11/2007 | Terentiev ............ B01F 3/04248 261/93 |
| 2009/0075362 A1* | 3/2009 | Baumfalk ............... B01L 3/505 435/289.1 |
| 2009/0139298 A1 | 6/2009 | Kiees et al. |
| 2011/0249526 A1* | 10/2011 | Wong ..................... B01F 7/162 366/142 |
| 2012/0160677 A1 | 6/2012 | Feng |
| 2012/0178153 A1 | 7/2012 | Feng et al. |
| 2012/0244609 A1 | 9/2012 | Selker et al. |
| 2012/0291238 A1* | 11/2012 | Barnfield Frej ....... C12M 23/14 24/572.1 |
| 2013/0145818 A1 | 6/2013 | Allgauer et al. |

\* cited by examiner

PH SENSOR FOR SINGLE USE EQUIPMENT

CROSS-REFERENCE TO RELATED APPLICATIONS

The present application is based on and claims the benefit of U.S. Provisional Patent Application Ser. No. 62/152,146 filed Apr. 24, 2015, the contents of which is hereby incorporated by reference in their its entirety.

BACKGROUND

Single use equipment alternatives provide a number of advantages for various industries. Typically, such equipment need not be cleaned and/or stored after use. Single use equipment can also reduce the machinery required for an industrial plant, for example sterilization equipment is not necessary. Further, single use equipment only requires manufacture to withstand a single use, often allowing for alternative, less expensive, material construction. Additionally, initial conditions provided by the manufacturer of such equipment, such as pre-sterilization, for example, can allow the single use equipment to be used without significant setup time or expense. One example of single use equipment is a single use container, such as a single use bioreactor.

Bioreactors are useful for generating and supporting biological reactions for any number of purposes. As a biological reaction progresses, the reaction itself may change a pH of the solution within the bioreactor. Monitoring or detecting pH can thus be highly useful in order to monitor the status and/or progression of a reaction. Accordingly, pH sensors are often used with single use bioreactors.

Detecting a pH of a reaction mixture is one of the most common process chemical measurements, particularly in the biologics industry. pH is a measure of a relative amount of hydrogen and hydroxide ions in an aqueous solution. In fermentation and cell culture, one of the most critical process challenges is to maintain an optimal pH level. Some biologic reactions, such as fermentation or culture processes, utilize a live organism such as a yeast, bacteria, or fungus strain to produce a desired active ingredient. Fermentation processes normally have a relatively short duration (2-7 days). Cell culture is a process in which a mammalian cell is grown to produce an active ingredient. The cell culture typically takes somewhat longer (2-8 weeks). The pH of a reaction mixture for these, or other example biologic reaction processes, often needs to be kept within an optimal range. The mixture becoming too acidic or too basic, for example, may result in a change in the reaction rate, production of unwanted byproducts or even premature death of the live organism driving the reaction.

One significant challenge for pH measurement in the fermentation and cell culture fields is the cleaning processes involved with the fermentation chamber or bioreactor. A fermentation or bioreaction chamber must be sterilized prior to a reaction process to ensure against cross-batch contamination of any unwanted growths. In addition, pH sensors typically undergo a two-point calibration using buffer solutions. Such cleaning can include steaming the fermenter or bioreactor as well as the pH sensor. Exposure to high temperatures, steam and rapid thermal shock can significantly affect the sensor's life.

SUMMARY

A single use pH sensor housing for a single user container is provided. The single use pH sensor housing includes a compartment configured to house a single use pH sensor. In one embodiment, the single use pH sensor housing comprises an actuator configured, when actuated, to transition the single use pH sensor from a storage position to a deployed position. In the storage position, the pH sensor is in fluidic contact with a buffer solution. In the deployed position, the single use pH sensor is in fluidic contact with an interior of the single use container. During the transition from the storage position to the deployed position, the buffer solution moves from a sensor portion of the compartment to a storage portion of the compartment such that the buffer solution is prevented from entering the interior of the single use container.

DETAILED DESCRIPTION OF ILLUSTRATIVE EMBODIMENTS

There exists an emerging need for a disposable pH sensor compatible with a plastic bag-type, ready-to-use, disposable bioreactor. Many glass electrode-based pH sensors require that the active surface or membrane of the sensor be protected from physical and environmental damage. This function is typically served by a disposable boot or cup placed over the sensing end of the pH sensor. However, reusable pH sensors require cleaning and sterilization prior to re-use in another bioreaction chamber. Further, pH sensors require calibration and storage in a buffer solution in order to ensure accurate measurements. However, it is desired to have a pH sensor that is compatible with single use bioreactors.

Embodiments of the present invention generally comprise a pH sensor configured to be installed on the wall of a single use bioreactor with a mechanical design that allows for a buffer, or booting solution, to be stored about the pH sensing and reference element during sterilization, storage, and shipment of the single use bioreactor. The mechanical design, however, in one embodiment, also allows the storage chamber retaining the booting solution to expose the sensing and reference element to a reaction fluid within the bioreactor. Additionally, in at least some embodiments, the sensor is also configured to retain the booting solution, such that the bioreactor is not contaminated by the booting solution when the pH sensor is deployed.

Figure 1:
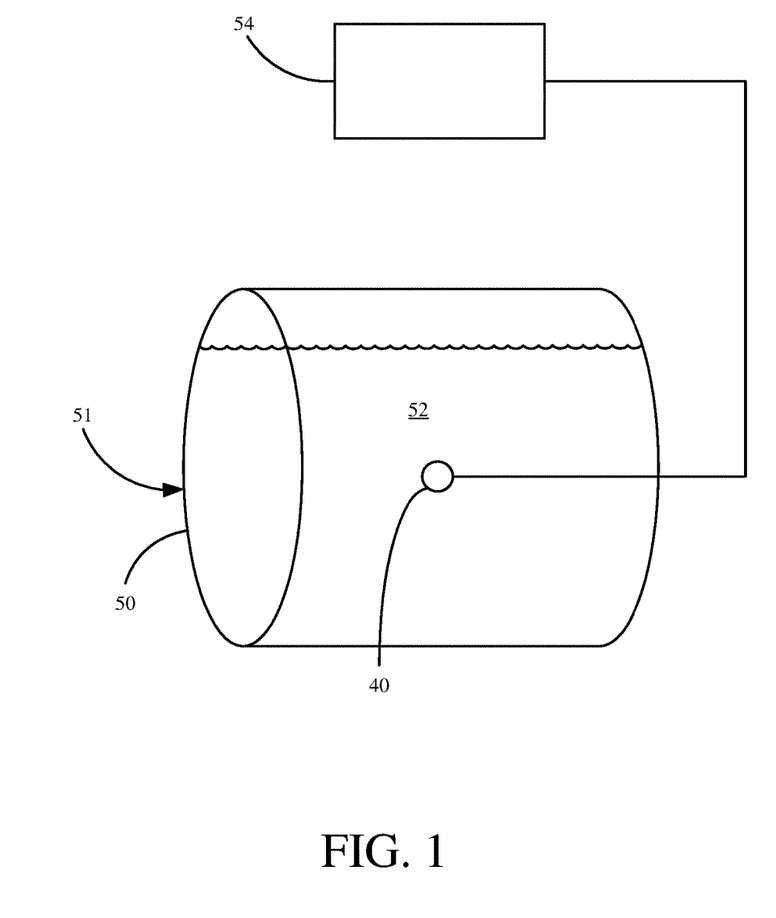
FIG. 1 is a diagrammatic view of a pH sensing bioreactor system with which embodiments of the present invention are particularly useful.

FIG. 1 is a diagrammatic view of a pH sensing bioreactor system with which embodiments of the present invention are particularly useful. In one embodiment, pH sensor 40 is electrically coupled to pH analyzer 54 which may comprise any suitable pH analyzer, or other appropriate electrical instrument. In one embodiment pH sensor 40 and pH analyzer 54 are coupled, for example through a wired connection. In another embodiment, pH sensor 40 and analyzer 54 are two parts of a single pH sensing apparatus.

pH sensor 40, in one embodiment, is physically attached to the wall 50 of a single use bioreactor 51. In another embodiment, pH sensor 40 is mounted within a port located within wall 50 of a single use bioreactor 51. A sample 52 is disposed within single use bioreactor 51 and it is monitored, or otherwise measured by pH sensor 40. In one embodiment, pH sensor 40 is only exposed to sample 52 at an operator's initiation. For example, pH sensor 40 may require actuation prior to engaging sample 52.

Figure 2A:
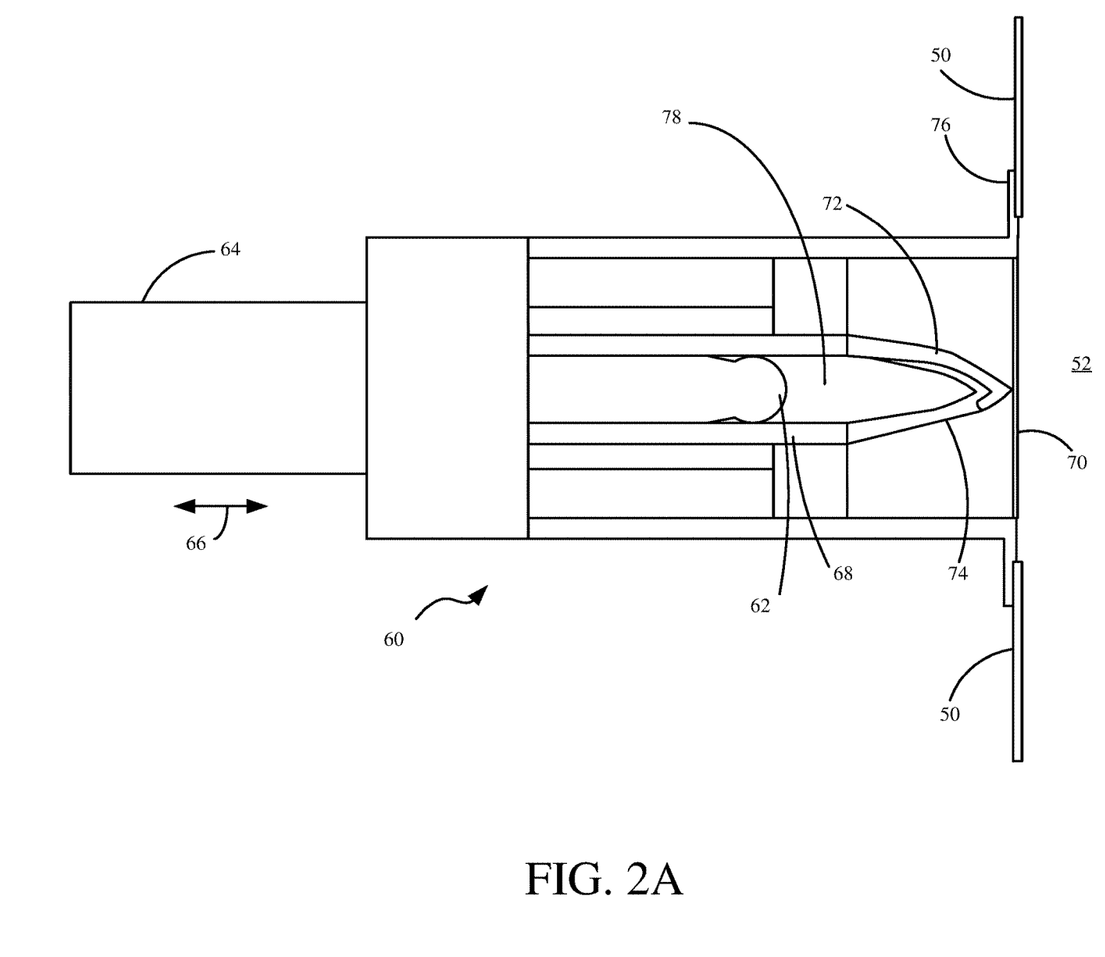
FIGS. 2A-2C include diagrammatic views of a pH sensor in accordance with an embodiment of the present invention.

FIG. 2A is a diagrammatic cross-sectional view of a pH sensor 60 in accordance with and embodiment of the present invention. pH sensor 60 is illustrated in FIG. 2A, in one embodiment, in a booted position. The booted position comprises a sensing element, such as electrode 62, located separated from, and not in contact with, sample 52. A booted position, in one embodiment, is a post-manufacturing position of sensor 60. In the booted position, sensing electrode 62 is exposed only to a buffer solution. At least some pH sensors benefit from regular calibration prior to use. Additionally, some pH sensors require consistent exposure to an aqueous solution, and can become inaccurate, or even non-functional, if left to dry out. The buffer solution 78 may, in one embodiment, be configured to provide the electrode 62 fluidic contact with an aqueous solution such that the electrode 62 does not dry out. However, many electrodes are not configured for storage in distilled water and, therefore, are stored with a buffer solution. The buffer solution may be, in one embodiment, a pH 7 buffer solution. In another embodiment, a pH 4 buffer solution may be used. However, the buffer solution 78 may comprise, in one embodiment, components that should not contaminate sample 52.

Figure 2B:
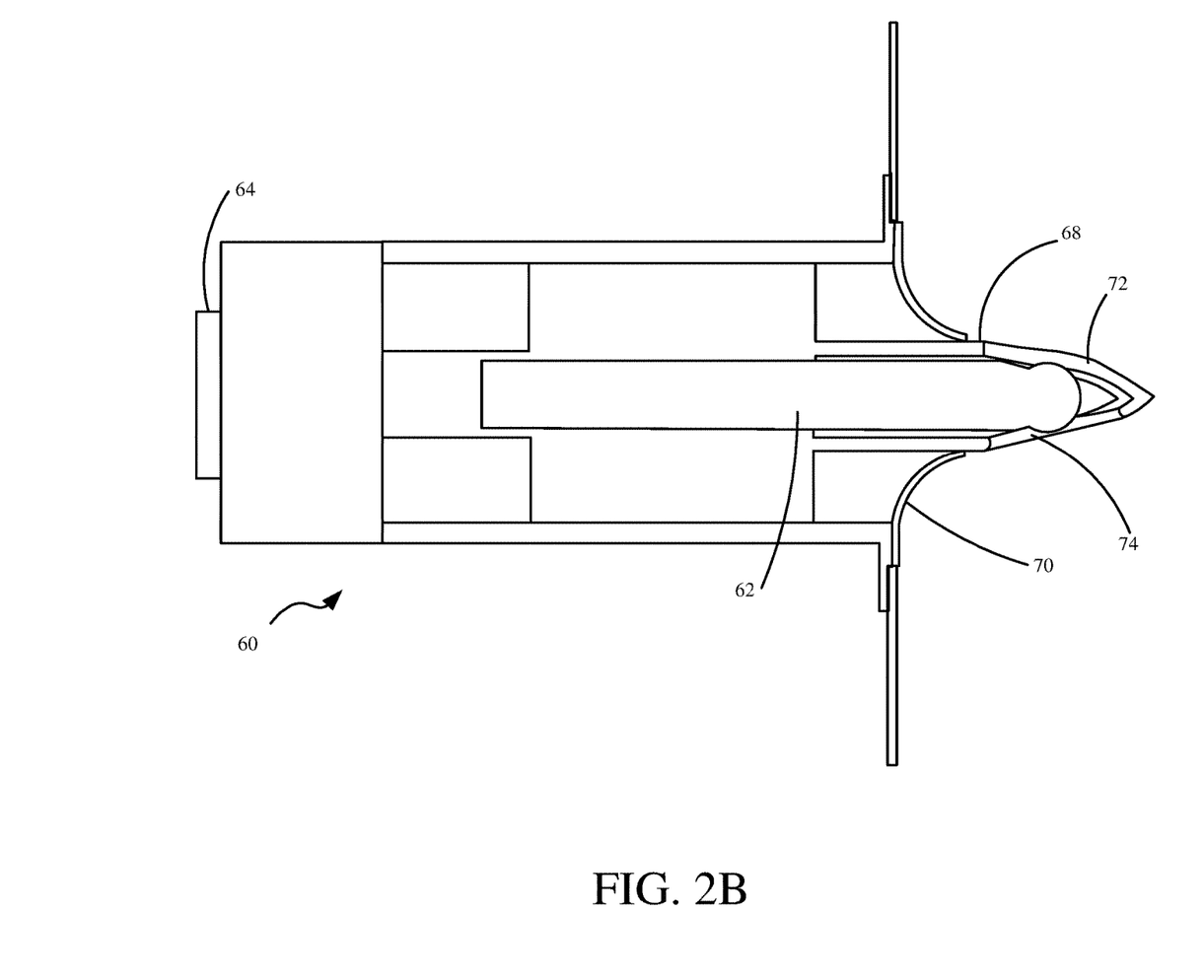

As used herein, sensing electrode 62 can comprise any electrode or portion of an electrode that may be exposed to a sample fluid and configured to provide an electrical response related to the sample fluid. Accordingly, a sensing electrode 62 is intended to include a glass bulb electrode and a reference junction. pH sensor 60 includes plunger 64 that is coupled to electrode 62 such that axial movement of plunger 64 in the direction indicated at reference numeral 66 will generate corresponding movement of electrode 62. Electrode 62 is disposed, in one embodiment, such that it is proximate, and can move into position with access spear 68. Access spear 68 is physically shaped like a spear such that activation of plunger 64 will cause access spear 68 to pierce through rubber membrane 70. When access spear 68 is pierced through rubber membrane 70, ports 72 and/or 74 allow a sample 52 to come into contact with electrode 62. When access spear 68 pierces rubber membrane 70, pH sensor 60 is said to be in a deployed position. Such configuration is illustrated in FIG. 2B. However, while a spear shaped access mechanism 68 is described, other mechanisms for providing contact between the electrode and a sample are also envisioned.

pH sensor 60, in one embodiment, comprises a flange 76 (shown in FIG. 2A) that is fused, adhered, or otherwise bonded to a portion of wall 50 of bioreactor 51. In the embodiment illustrated in FIG. 2A, flange 76 is bonded to the outer surface of wall 50. However, embodiments of the present invention also envision flange 76 being bonded to an inside surface of wall 50. Flange 76 can be thermally welded, or otherwise permanently attached, to side wall 50 of bioreactor 51 in any suitable manner. The attachment of flange 76 to wall 50 may be accomplished, in one embodiment, by a manufacturer such that a sterile environment is maintained within bioreactor 51. In another embodiment, flange 76 is configured for bonding, by an operator of the bioreactor 51, as an after-market attachment procedure.

Figure 2C:
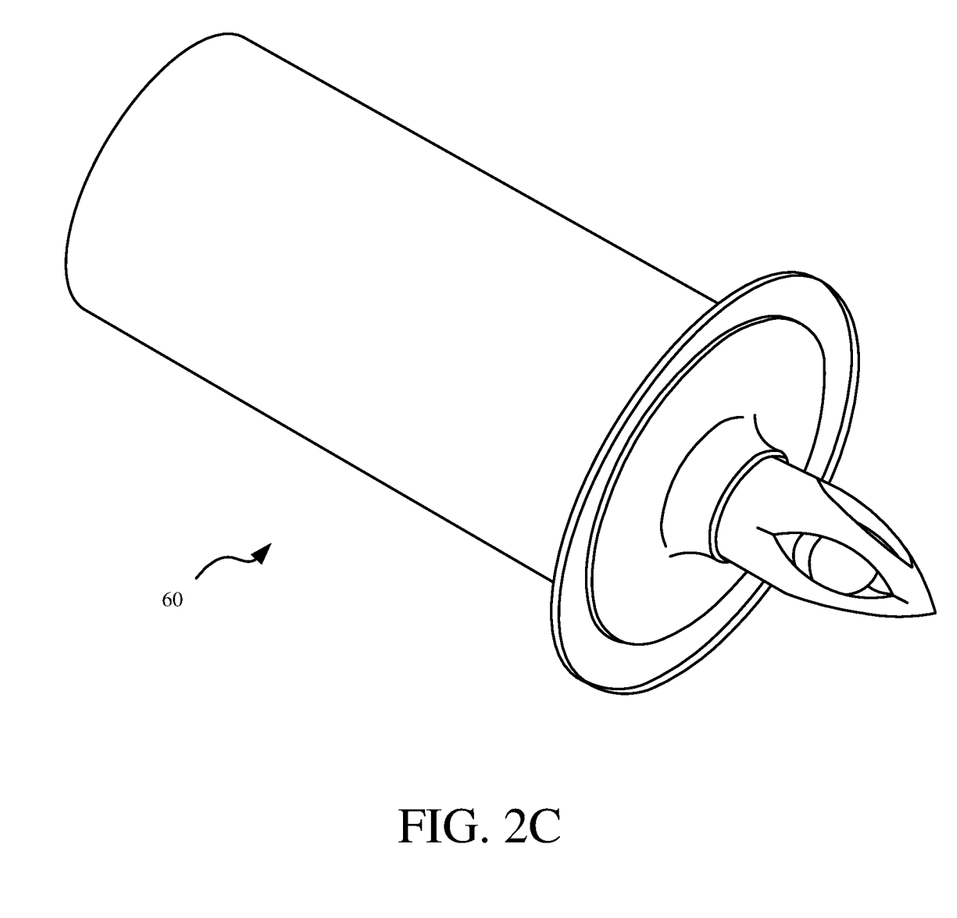

FIG. 2C is a diagrammatic perspective view of pH sensor 60 in accordance with one embodiment of the present invention, shown for example in a deployed position. It is noted, that for at least some reactions, the calibration fluid within a pH sensor should not come into contact with a reaction sample. For example, the calibration solution may not be inert with respect to some or all of the reactants within a reactant sample. Additionally, the calibration solution may comprise a pH that would alter the pH of sample 52. For that reason, it may be desired to allow for contact between sensor 62 and reaction sample 52 such that calibration fluid 78 is kept separate from sample 52.

A pH sensor for a typical single use bioreactor contains a storage and/or calibration solution that, when the pH sensor is actuated, enters the bioreactor. In some cases, the buffer solution will contaminate, and interfere with, a culture or fermentation process occurring within the bioreactor. Embodiments of the present invention generally provide a system that maintains a buffer for the pH sensing electrode 62 in a booted position, and prevents the buffer 78 from contacting a sample 52 in a deployed position. Specifically, embodiments of the present invention generally capture or otherwise contain buffer 78 such that it cannot engage sample 52 within single use reactor 51.

Figure 3A:
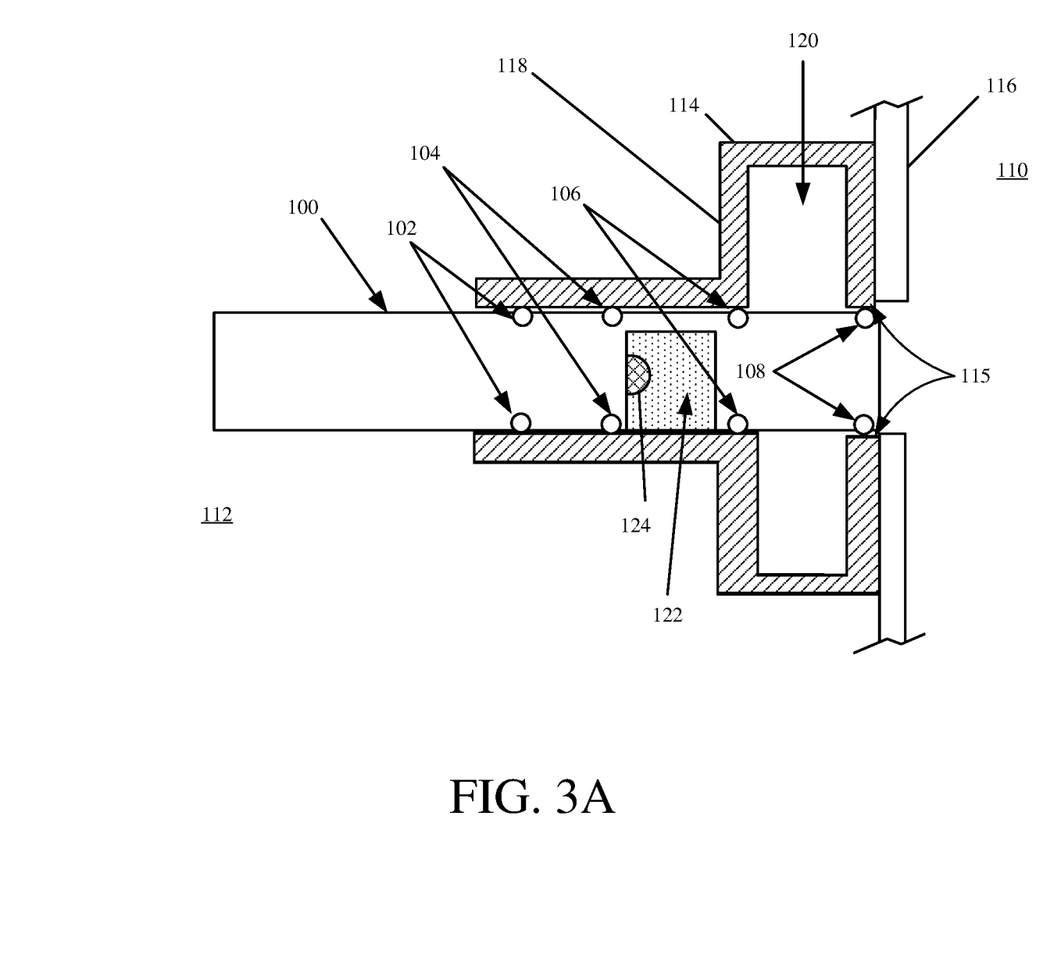
FIGS. 3A-3D are cross-sectional views of a pH sensor in different configurations in accordance with an embodiment of the present invention.
Figure 3B:
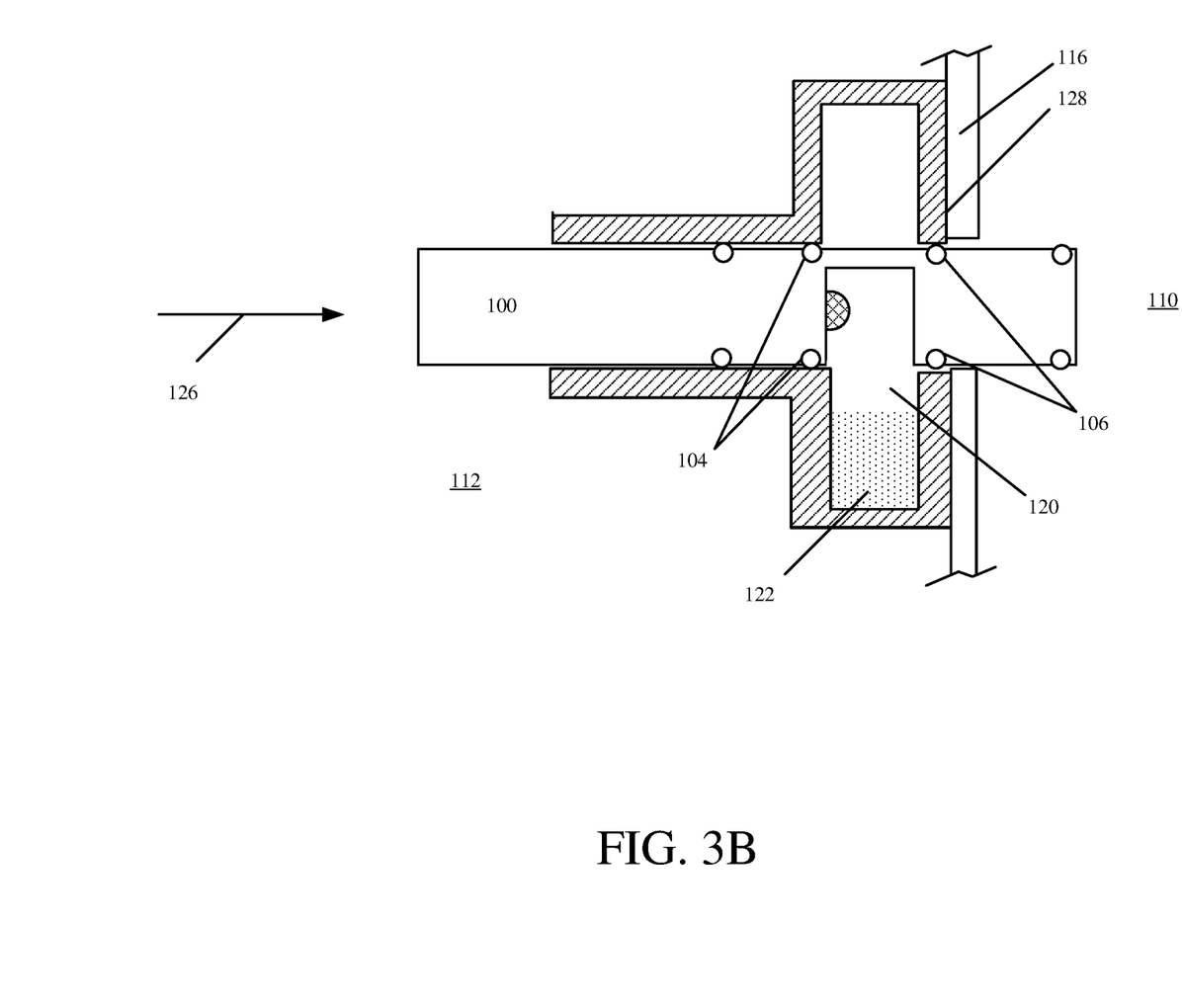
Figure 3C:
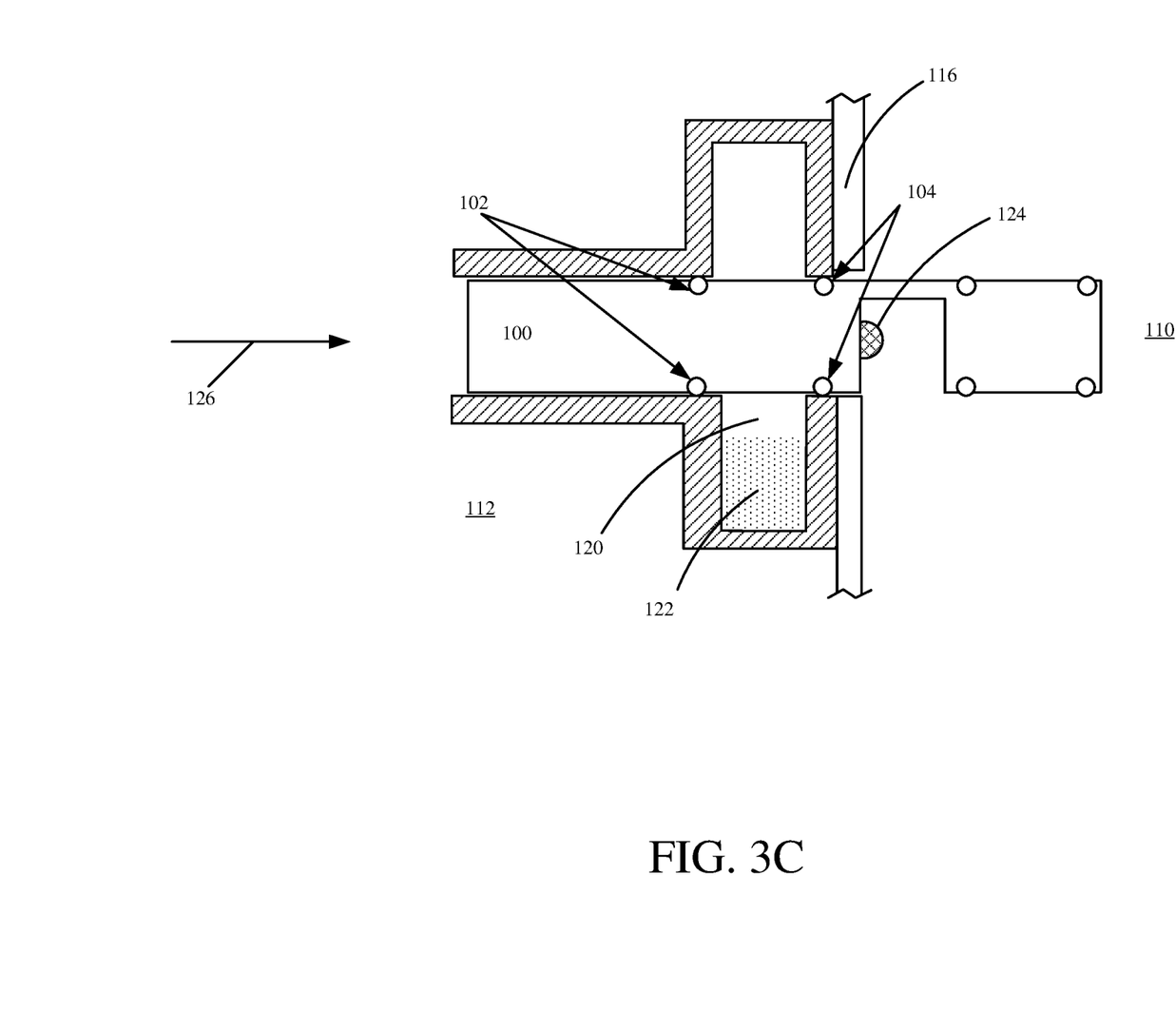

FIGS. 3A-3C are cross-sectional views of a pH sensor in different configurations in accordance with an embodiment of the present invention. pH sensor 100, in one embodiment, is coupled to a sensor port 114 on a wall 116 of a bioreactor interior 110.

FIG. 3A is a cross-sectional view of pH sensor 100 coupled to a sensor port 114 of a bioreactor bag while pH sensor 100 is in a storage or calibration configuration. pH sensor 100, in the embodiment illustrated in FIG. 3A, comprises a cylindrical shape similar to that of sensor 60, illustrated in FIG. 2C. Sensor 100, in one embodiment, includes a number of O-ring seals 102, 104, 106, 108 disposed about its outer diameter. While four O-ring seals 102, 104, 106 and 108 are illustrated, in another embodiment sensor 100 comprises additional O-ring seals spaced closer together, for example, 6 O-ring seals or 8 O-ring seals spaced evenly along a shaft of the sensor 100. In at least one embodiment, redundant O-ring seals are included in order to ensure complete containment of a buffer solution as the sensor 100 moves from a booted position to a deployed position, for example.

O-ring seals 102, 104, 106 and 108, in one embodiment, engage an inner diameter of sensor port 114 such that they maintain a seal. The seal maintained between O-rings 102-108 and port 114 is configured, in one embodiment, such that an interior of the single use bioreactor 110, is isolated from the ambient environment.

Sensor port 114 may be formed of any suitable material. In one embodiment, sensor port 114 is formed of a material that may be thermally welded to wall 116 of the single use bioreactor. In one embodiment, sensor port 114 comprises the same material as wall 116. In another embodiment, sensor port 114 comprises a different material from wall 116. In one embodiment, sensor port 114 and wall 116 are plastic. While the example shown in FIG. 3A has sensor port 114 affixed to an outer surface of a wall 116, it is expressly contemplated that embodiments of the present invention can be practiced where a portion of sensor port 114 passes through an aperture of wall 116, and that surface 118 of sensor port 114 can be affixed to an inner surface of wall 116.

In one embodiment, after port 114 is welded to wall 116, the reactor apparatus undergoes a sterilization process.

In the booted position shown in FIG. 3A, O-ring 108 bears against the inner surface 115 of sensor port 114, forming a seal between pH sensor 100 and an interior 110 of the bioreactor. Additionally, in one embodiment, O-ring 106 bears against a different portion of inner surface 115 of sensor port 114, forming a sealed space such that calibration solution 122 is trapped within a buffer space in a booted position, and trapped within a space 120 in a deployed position, as illustrated in FIG. 3B. Solution 122, in one embodiment is a storage solution meant to protect and maintain sensing element 124 during shipping and handling. In one embodiment, solution 122 is a buffer solution with a known pH. In one embodiment, solution 122 comprises one or more buffering elements configured to maintain a consistent pH around sensing element 124, and to ensure that sensing element 124 does not dry out prior to use. Thus, solution 122 may be referred to as either a storage or calibration solution, even though embodiments of the present invention can be practiced without using solution 122 as a calibration mechanism for sensing element 124.

O-rings 102 and 104 bear against the inner surface of sensor port 114, and maintain a seal such that solution 122 cannot leak into the ambient environment in either a booted or deployed position. In one embodiment, in a fully deployed position, O-rings 102 and 104 provide a seal around space 120 such that captured solution 122 cannot contaminate a sample within interior 110 or be released into ambient space 112.

FIG. 3B is a cross-sectional view of a pH sensor coupled to a sensor port of a bioreactor bag while the pH sensor is in a solution trapping configuration. In one embodiment, pH sensor 100, when actuated, may transition from a storage position to a deployed position and pass through a solution trapping configuration, such as that illustrated in FIG. 3B. In one embodiment, pH sensor 100 does not stop forward movement in the solution trapping configuration, but moves from a booting position to a deployed position in a single motion. In another embodiment, the pH sensor 100 is configured to stop upon reaching the solution trapping configuration in order to provide sufficient time for the solution 122 to flow into space 120. In the transition from booted position shown in FIG. 3A to solution-trapping configuration shown in FIG. 3B, pH sensor 100 has moved axially in the direction indicated by arrow 126 such that the solution 122 is free to flow into solution trapping space 120 within sensor port 114.

In the solution trapping configuration, illustrated in FIG. 3B, O-ring 106 contacts a portion of interior surface 115 of sensor port 114, forming a seal between bioreactor interior 110 and solution trapping space 120, such that solution 122 cannot contaminate a sample within interior space 110. In one embodiment, O-ring 104 also contacts an interior surface 115 of sensor port 114 such that solution 122 cannot leak into an ambient space 112. In one embodiment, as illustrated in FIG. 3B, in the solution trapping configuration, O-ring 108 is disposed within interior 110.

FIG. 3C is a cross-sectional view of pH sensor 100 coupled to sensor port 114 of a bioreactor bag while pH sensor 100 is in an active, or deployed, configuration. In one embodiment, transitioning pH sensor from a booted configuration to an activated configuration, as illustrated in the transition from FIG. 3A to FIG. 3C, comprises pH sensor 100 moving axially along the direction of arrow 126. In one embodiment, a single movement is necessary to transition pH sensor 100 between the positions illustrated in FIGS. 3A and 3C. In another embodiment, transitioning from a booted to a deployed position comprises first transitioning from a booted to a solution trapping configuration, and then transitioning from the solution trapping configuration to the active, or deployed, position. The may comprise, in one embodiment, translating sensor 100 further along the direction of arrow 126 to achieve the position shown in FIG. 3C, as compared to the configuration shown in FIG. 3B, for example.

In a deployed configuration, such as that shown in FIG. 3C, sensing element 124 is fluidically coupled to interior 110 of the bioreactor. Thus, in the deployed configuration, pH sensor 100 is available to sense the pH of the contents within the bioreactor. However, in the transition from the solution trapping configuration of FIG. 3B to the deployed position of FIG. 3C, buffer solution 122 remains trapped within space 120.

In one embodiment, in the deployed configuration illustrated in FIG. 3C, O-ring 104 bears against the inner surface 115 of sensor port 114 such that it forms a seal between interior 110 and solution trapping space 120. In one embodiment, O-ring 102 simultaneously bears against the interior surface 115 of sensor port 114 such that it forms a seal between space 120 and ambient environment 112. In one embodiment, in the deployed configuration illustrated in FIG. 3C, O-rings 106 and 108 are exposed to a sample within interior 110.

Embodiments shown in FIGS. 3A-3C, described above, and 4A-4C, described below, appear to show the possibility that the solution trapping space could be fluidically coupled directly to an interior of a bioreactor while the pH sensor is moving from the solution trapping configuration to the active configuration. However, this is simply due to an exaggeration of the dimensions in order to clearly illustrate the different configurations. In at least one embodiment, an O-ring, for example O-ring 106, will maintain a seal between a reactor interior and a solution trapping space until another O-ring, for example O-ring 104, assumes the same function. Thus, the thickness of a most distal wall, for example wall 128, has a dimension that is larger than the axial space between O-rings 104 and 106 along the length of a sensor, for example sensor 100.

Figure 3D:
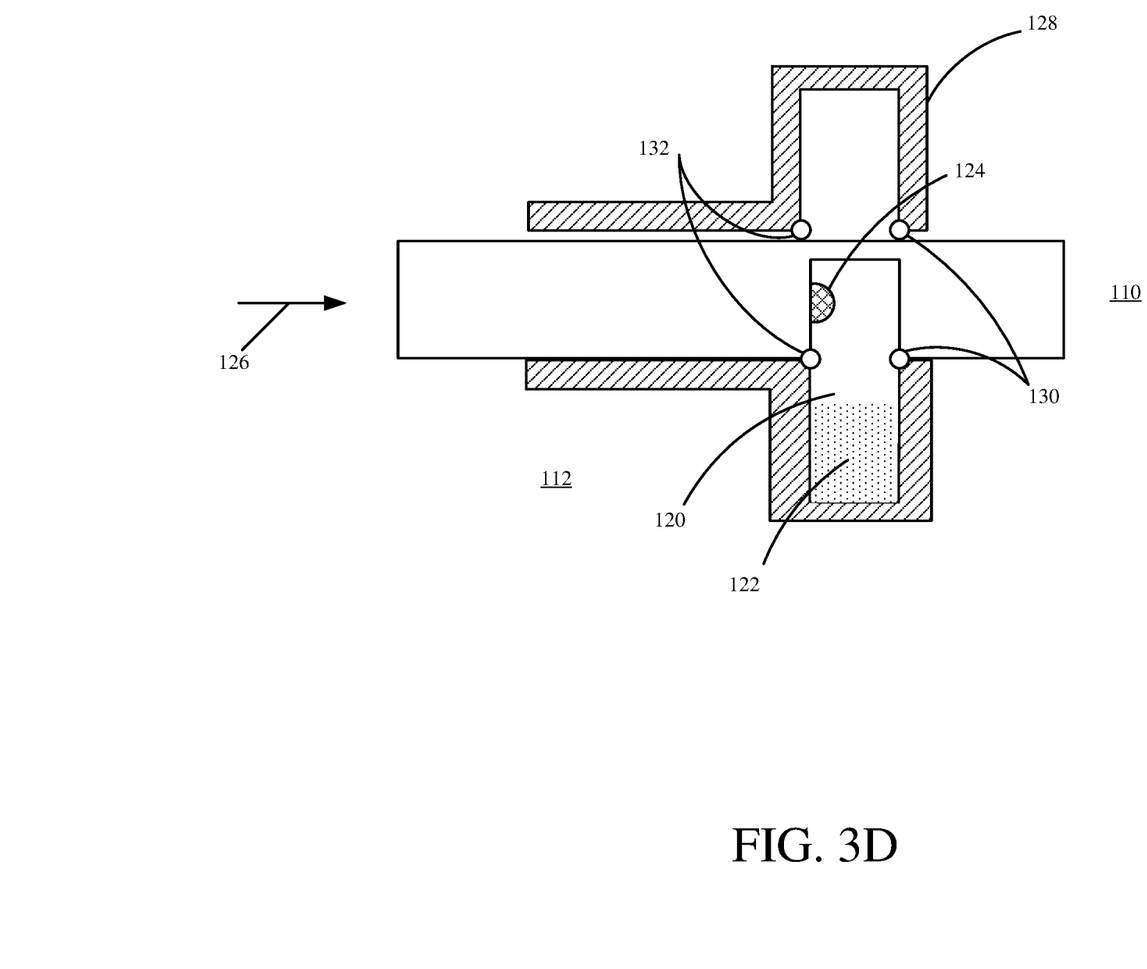

FIGS. 3A-3C illustrate an embodiment where a plurality of O-rings 102-108 are fixed to a sensor 100. However, in another embodiment, as illustrated in FIG. 3D, a plurality of O-rings 132 and 130 are, instead, fixed to the interior of port 114 such that, as the sensor 100 moves axially along direction 126, buffer solution 122 come into fluidic contact with, and transfers to space 120. In one embodiment, O-ring 132 provides a seal between space 120 and ambient space 112 such that solution fluid 122 cannot leak out of pH sensor 100 into the ambient environment. In one embodiment, O-ring 130 provides a seal between space 120 and interior 110 such that solution fluid 122 cannot contaminate a sample within the bioreactor.

Figure 4A:
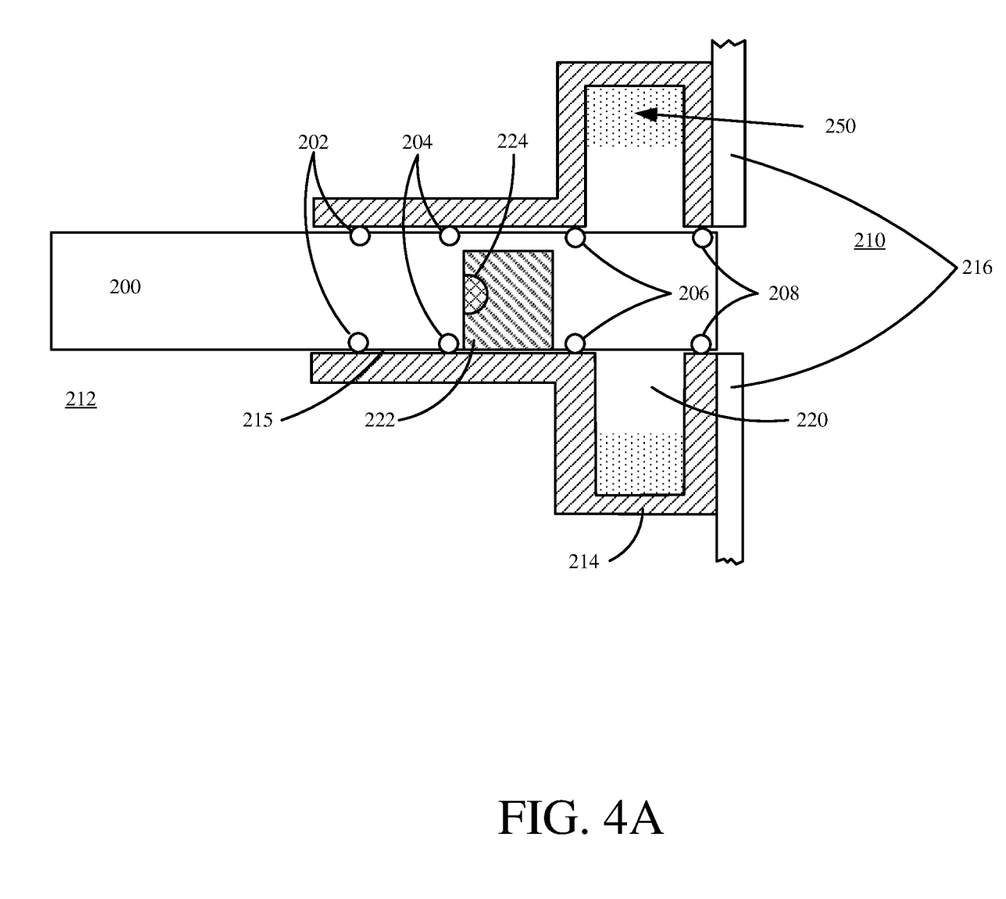
FIGS. 4A-4C are cross-sectional views of a pH sensor in different configurations in accordance with a second embodiment of the present invention.
Figure 4B:
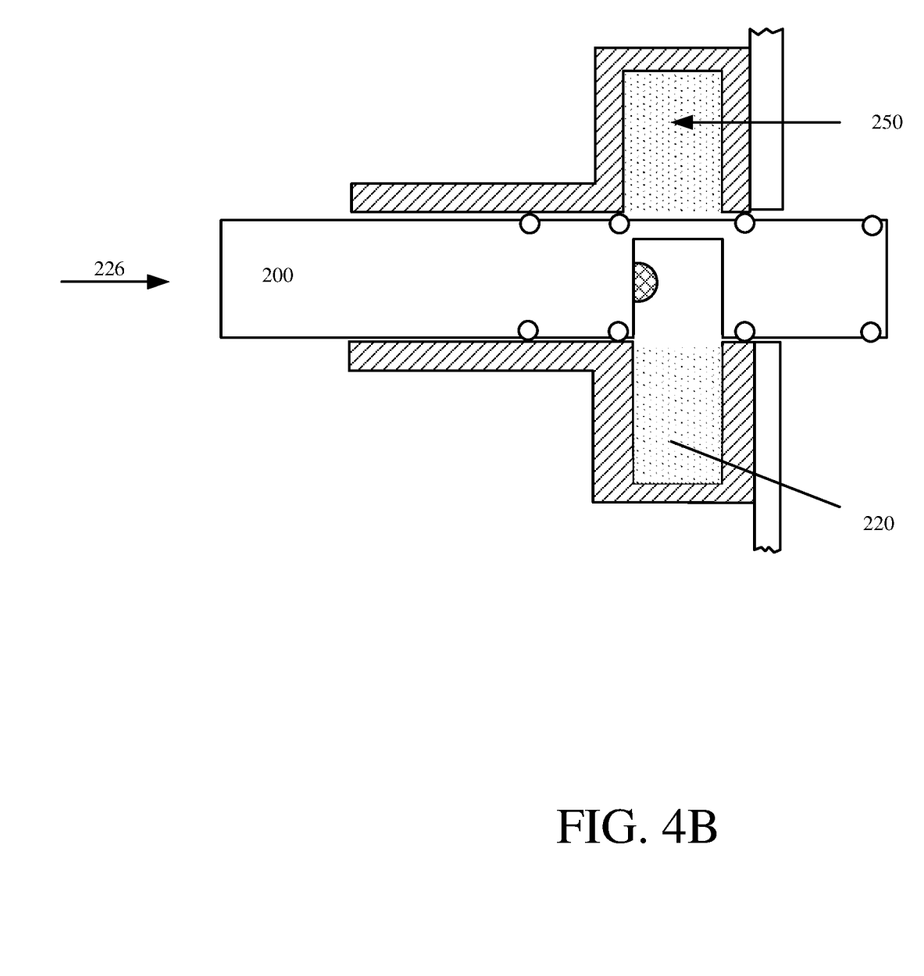
Figure 4C:
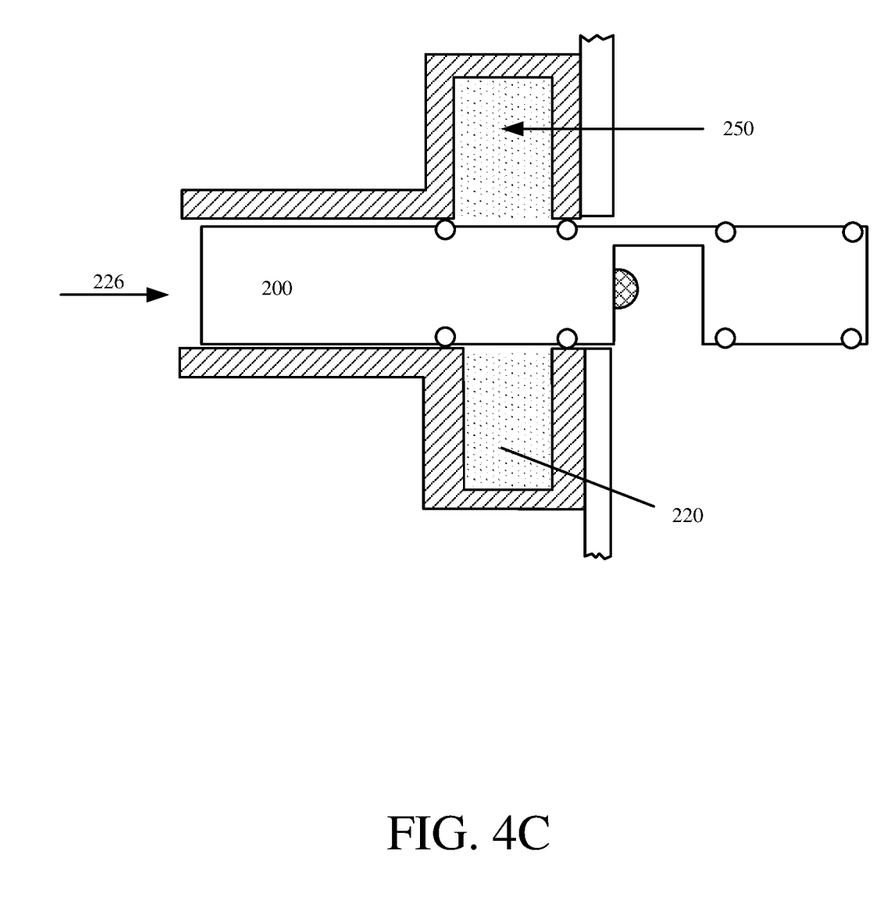

FIGS. 4A-4C are cross-sectional views of a pH sensor in different configurations in accordance with another embodiment of the present invention. FIGS. 4A-4C may bear some similarities to FIGS. 3A-3C and like components are numbered similarly. However, in one embodiment, a solution trapping space 220 of pH sensor 200 is at least partially filled with an absorbent material 250. In one embodiment, absorbent material 250 is configured to facilitate the capture of solution 222 when pH sensor 200 is placed in the solution trapping configuration, for example as shown in FIG. 4B. Absorbent material 250 may be configured, in one embodiment, to at least partially absorb solution 222. In one embodiment, absorbent material 250 is a synthetic polymer, for example a copolymer. In one embodiment, absorbent material 250 comprises a slush powder or a superabsorbent polymer (SAP) configured to absorb and retain large amounts of fluid relative to a dry mass of the powder. In another embodiment, absorbent material 250 comprises a fibrous resin, cellulosic or fiber-based, for example a sponge, pulp, a cotton plug, etc. In one embodiment, absorbent material comprises a gel configured to absorb fluid 222. In one embodiment, absorbent material 250, prior to contact with solution 222, fills only a portion of space 220, and is configured to expand after absorbing solution 222.

In one embodiment, pH sensor 200 comprises a plurality of O-rings configured to maintain a seal between solution 222 and both the ambient environment 212 and interior 210, for example O-rings 202 and 208. In one embodiment, O-rings are only necessary to maintain a seal about a sensing element 224, such that sensing element 224 cannot dry out, for example O-rings 204 and 206. In one embodiment, a plurality of O-rings are fixed to an interior surface 215 of port 214, for example to ensure that solution 222 is received within and trapped in space 220, as pH sensor 200 moves between a storage and a deployed position.

FIG. 4B illustrates a solution-trapping configuration of sensor 200. In one embodiment, as sensor 200 moves from a storage position, for example as shown in FIG. 4A, to a deployed position, for example as shown in FIG. 4C, it moves through solution-trapping configuration as shown in FIG. 4B.

FIG. 4C illustrates a deployed configuration for sensor 200. In one embodiment, sensor 200 transitions from a storage configuration, for example FIG. 4A, to a deployed configuration, for example FIG. 4C, by actuating a movement mechanism such that sensor 200 moves axially along the direction indicated by arrow 226. In one embodiment, the actuation mechanism comprises a manual plunger activated by a user. In one embodiment, actuation of the actuation mechanism triggers a smooth transition between the storage and deployment configurations. In another embodiment, actuation of the actuation mechanism triggers a series of transitions, for example from the storage to the solution-trapping configuration, and then from the solution-trapping configuration to the deployed configuration. In one embodiment, additional force is required to cause an access spear to break through a wall 216, for example additional pressure on a manual plunger.

Figure 5:
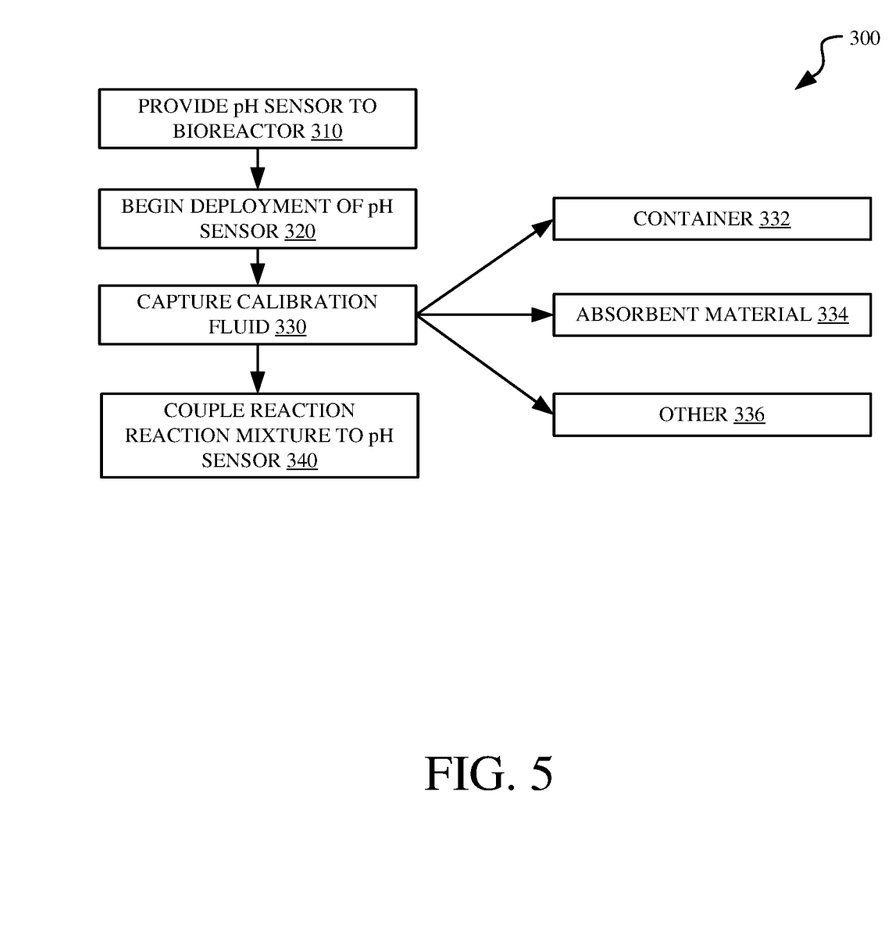
FIG. 5 illustrates a method of providing a pH sensor of measuring a pH within a bioreactor configurations in accordance with one embodiment of the present invention.

FIG. 5 illustrates a method of measuring a pH within a bioreactor in accordance with one embodiment of the present invention. Method 300 may be utilized with any suitable reaction chamber, but may be particularly useful with a reaction chamber configured to house a biological reaction.

In block 310, a pH sensor is provided to a bioreactor. In one embodiment, the pH sensor is manufactured along with the bioreactor and shipped to a user as a single unit. However, in another embodiment, the bioreactor is manufactured with a sensor port, and providing the pH sensor to the bioreactor, as illustrated in block 310 comprises coupling a pH sensor to the bioreactor through the sensor port. In one embodiment, the pH sensor is provided to the bioreactor such that a sensing element is exposed to a pH buffering solution, where the pH buffering solution is configured to maintain fluidic contact with the pH sensor.

In block 320, deployment of the pH sensor beings. Deployment may comprise, in one embodiment, transitioning the pH sensor from a storage position to a deployed position. Deployment can include a portion of the pH sensor breaching a wall of a bioreactor. Deployment can also include actuation of a plunger to move the pH sensor axially toward the bioreactor. In one embodiment, deployment comprises activating a screw-type plunger that, as it rotates along a threaded track, urges the pH sensor towards the sample within the bioreactor. In one embodiment, the pH sensor is provided, for example through a port, such that it is separated from a reaction fluid by a wall of the bioreactor bag. In another embodiment, there is no separating wall, but a portion of the pH sensor provides a barrier, for example an O-ring as illustrated in FIGS. 3 and 4.

In block 330, the calibration or storage solution initially provided around a sensing element is collected such that it cannot come into fluidic contact with a sample within the bioreactor. Capturing the calibration solution can be accomplished in a variety of ways, for example removal to a separate container 332, removal by absorbent material 334, or another removal mechanism. For example, in one embodiment, the pH calibration solution is otherwise ejected from the pH sensor a provided to a waste bin. In another embodiment, the pH calibration solution is absorbed by an absorbing material.

In block 340, the pH sensor engages a reaction mixture within a reaction chamber. Fluidic engagement of the pH sensor with the reaction mixture may comprise, for example the pH sensor breaking through a wall of the reactor bag, as described above with regard to FIGS. 2A-2C, or may comprise a chamber opening and exposing the pH sensor the reaction mixture, as illustrated in FIGS. 3 and 4. In one embodiment, fluidic engagement of the pH sensor happens proximate removal of sensor fluid such that the pH sensor does not dry out prior to engaging the reactor sample.

While embodiments described herein have generally focused the selection of different sensor configurations via relative movement between a sensor and a sensor port on a bioreactor, other forms of movement can be used as well. For example, embodiments of the present invention can be practiced where the configurations are selected by rotating a sensor relative to a sensor port. Further still, combinations of axial and rotational movement could also be used in accordance with embodiments of the present invention.

Although the present invention has been described with reference to preferred embodiments, workers skilled in the art will recognize that changes may be made in form and detail without departing from the spirit and scope of the invention.

What is claimed is:

1. A single use pH sensor housing for a single use container, comprising:
   a compartment configured to house a single use pH sensor;
   an actuator configured, when actuated, to transition the single use pH sensor from a storage position to a deployed position;
   wherein in a storage position, the pH sensor is in fluidic contact with a buffer solution and wherein, in a deployed position, the single use pH sensor is in fluidic contact with an interior of the single use container; and
   wherein, during the transition from the storage position to the deployed position, the buffer solution moves from a sensor portion of the compartment to a trapping portion of the compartment such that the buffer solution is prevented from contacting the interior of the single use container.

2. The single use pH sensor housing of claim 1, wherein the housing is coupled to the single use container.

3. The single use pH sensor housing of claim 2, wherein the housing is fused to a portion of the single use container.

4. The single use pH sensor housing of claim 2, wherein the housing is coupled to the single use container through a sensor port on a wall of the single use container.

5. The single use pH sensor housing of claim 1, wherein the trapping portion of the compartment comprises an absorbent compound.

6. The single use pH sensor housing of claim 5, wherein the absorbent compound comprises a polymer.

7. The single use pH sensor housing of claim 1, and further comprising:
   a seal configured to maintain the isolation between the buffer solution and the interior of the single user container.

8. The single use pH sensor housing of claim 7, wherein the seal comprises an O-ring.

9. The single use pH sensor housing of claim 1, wherein actuation comprises movement of the pH sensor in an axial direction.

10. The single use pH sensor housing of claim 1, wherein actuation comprises breaching a wall of the single use container.

* * * * *